United States Patent [19]
Morgart et al.

[11] Patent Number: 5,171,134
[45] Date of Patent: Dec. 15, 1992

[54] PULSE DAMPENER AND ASSOCIATED METHOD

[75] Inventors: James R. Morgart, Stillman Valley; Ronald D. Picht, Rockford, both of Ill.

[73] Assignee: Alcoa Separations Technology, Inc., Warrendale, Pa.

[21] Appl. No.: 630,487

[22] Filed: Dec. 20, 1990

[51] Int. Cl.$^5$ .............................................. F04B 11/00
[52] U.S. Cl. ...................................... 417/540; 417/542
[58] Field of Search ................................ 417/540, 542

[56] References Cited

U.S. PATENT DOCUMENTS

| | | | |
|---|---|---|---|
| 2,216,374 | 10/1940 | Martin | 73/706 |
| 2,474,512 | 6/1949 | Bechtold et al. | 417/540 |
| 2,852,033 | 9/1958 | Orser | 137/115 |
| 2,883,180 | 4/1959 | Moulton | 267/35 |
| 3,146,724 | 9/1964 | Cornelsen | 417/540 |
| 3,474,830 | 10/1969 | Hertell | 138/30 |
| 4,427,029 | 1/1984 | Charney et al. | 138/30 |
| 4,548,713 | 10/1985 | Schmid | 210/198.2 |
| 4,587,993 | 5/1986 | Härtl | 138/30 |
| 4,624,625 | 11/1986 | Schrenker | 417/20 |
| 4,629,562 | 12/1986 | Kercher | 417/540 |

FOREIGN PATENT DOCUMENTS 2529290 12/1983 France ............................... 417/540

Primary Examiner—Richard A. Bertsch
Assistant Examiner—Charles G. Freay
Attorney, Agent, or Firm—Douglas G. Glantz

[57] ABSTRACT

A pulse dampener for use in a pumping system including a reciprocating pump comprising a body having a cavity formed therein and a cover for sealed connection with the body. A diaphragm is secured between the body and the cover for sealing the cavity from said cover. The cover includes an inlet and outlet and the cover and the diaphragm cooperate to define a liquid flow path through the pulse dampener. The body also includes a gas inlet means for receiving gas into a chamber defined by the cavity and the diaphragm. A gas is supplied into the chamber such as to provide a smooth flow through the pumping system. An associated method is also provided.

25 Claims, 3 Drawing Sheets

PULSE DAMPENER AND ASSOCIATED METHOD

BACKGROUND OF THE INVENTION

1. Field of the Invention

This invention relates to a pulse dampener and an associated method and more particularly to an apparatus and method that reduces the effect of pulsations of a liquid flow in a pumping system which includes a reciprocating pump.

2. Background Information

Pulse dampeners are used to absorb pulsations of liquid flow from reciprocating pumps in pumping systems. Known pulse dampeners are constructed with a cover and body separated by an elastic membrane. The body has a cavity which contains a dampening fluid. A temporarily increased feed of fluid results in a pressure rise which is absorbed by the dampening fluid via the elastic partition. If less fluid is conveyed temporarily, the pressure sinks and the damping fluid expands and compensates for the lacking volume.

Pulse dampeners are used extensively in liquid chromatography systems. See, e.g., U.S. Pat. Nos. 4,427,029; 4,629,562; 4,587,993; and 4,548,713. U. S. Pat. No. 4,548,713, for example, discloses a pulse dampener including a body portion having a cavity containing a compliant elastomer medium.

U.S. Pat. No. 4,624,625 discloses a high pressure metering pump including a pulsation damper (FIG. 4). The pulsation damper includes a diaphragm which separates an elastic liquid 67 from the damping volume 61. As pressure of the damping volume 61 increases, liquid 67 is compressed and diaphragm 63 bends towards liquid 67 thus causing an enlargement of damping volume 61. The enlargement, it is said, corresponds to the liquid volume maximally delivered to the pump during one cycle.

Prior art systems, such as those shown, typically operate at high pressures on the order of 1000-3000 psi. These pulse dampeners have been found to be ineffective at lower pressures such as between 0-300 psi.

There is a need for a pulse dampener that is effective in chromatography systems involving lower pressures such as between 0-300 psi.

SUMMARY OF THE INVENTION

The pulse dampener and associated method of the invention has met the above need. The pulse dampener is used in a pumping system including a reciprocating pump and comprises a body having a cavity formed therein and a cover for sealed connection with the body. A diaphragm is secured between the body and the cover for sealing the cavity from said cover. The cover includes an inlet and outlet and the cover and the diaphragm cooperate to define a liquid flow path through the pulse dampener. The body also includes a gas inlet means for receiving gas into a chamber defined by the cavity and the diaphragm. A gas is supplied into the chamber such as to provide a smooth liquid flow through the pumping system. An associated method is also provided.

It is an object of the invention to provide a pulse dampener that is effective in pumping systems having pressures of 0-300 psi.

It is a further object of the invention to provide a pulse dampener having chamber defined by an insert having a recess and an overlying diaphragm.

It is a further object of the invention to provide that the chamber volume is approximately equal to the volume of liquid pumped by one stroke of the reciprocating pump.

It is a further object of the invention to dampen the liquid flow pulsations in a pumping system by using a gas.

It is a further object of the invention to resist back mixing and to assure constant flushing of the internal volume of the pulse dampener.

These objects and other object of the invention will be fully understood from the following description of the invention with reference to the drawings appended to this Application.

DESCRIPTION OF THE PREFERRED EMBODIMENTS

Figure 1:
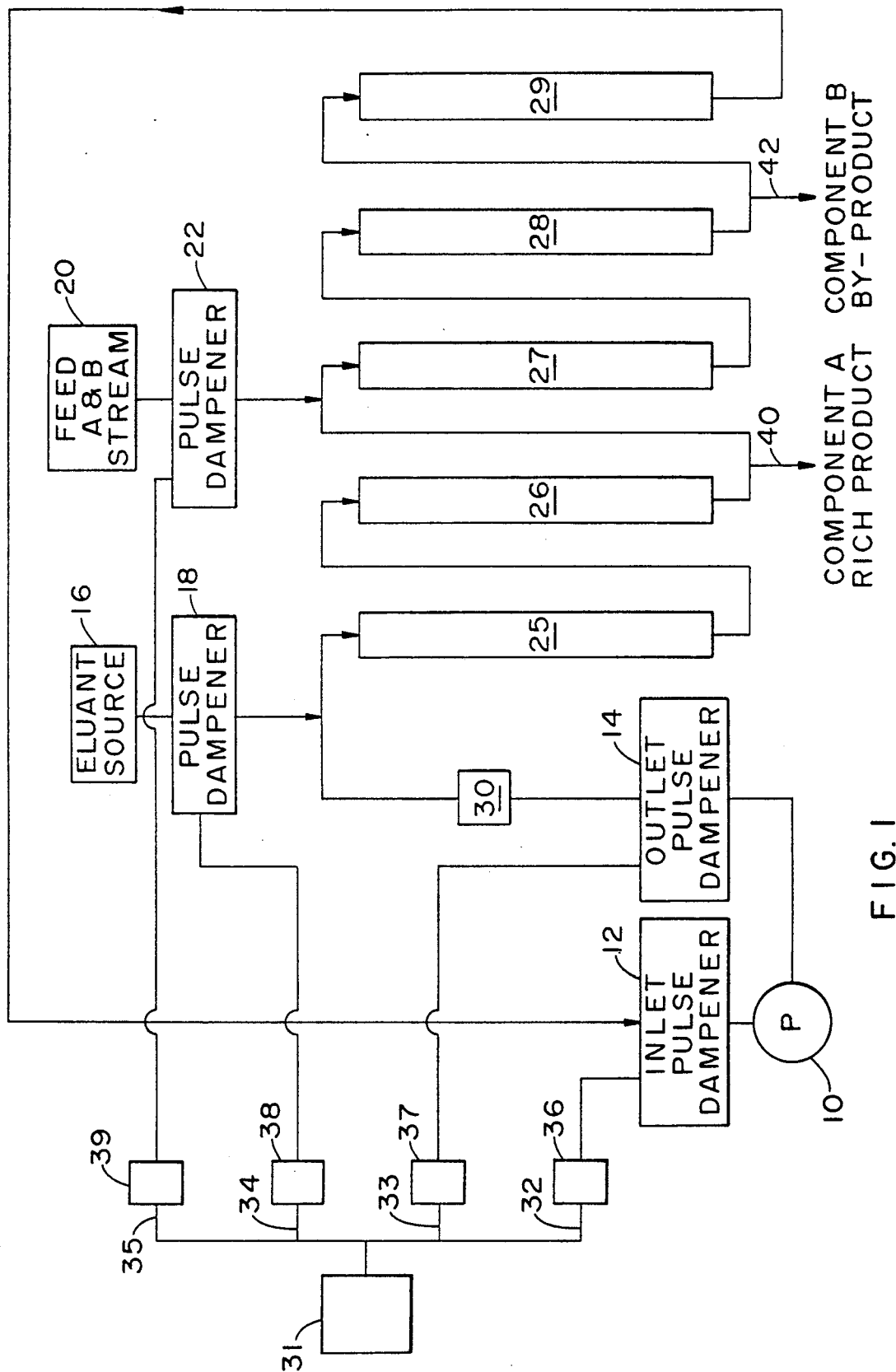
FIG. 1 is a schematic diagram of a chromatography system in which the pulse dampener of the invention can be used.

FIG. 1 shows a schematic diagram of a chromatography system in which the pulse dampener of the invention can be used.

The system consists of a reciprocating pump 10, inlet pulse dampener 12 and outlet pulse dampener 14. The reciprocating pump 10 typically operates at 2-300 strokes/minute with each stroke pumping a volume of 0.5 cc. The system further consists of an eluant source 16 that introduces an eluant into another pulse dampener 18 and eventually into the system. The feed stream source 20 introduces a mixture of components "A" and "B" through a pulse dampener 22 into column 27, which is one of the five columns 25, 26, 27, 28 and 29 in this system. The feed stream source 20 advances from column to column. Hence, this is a continuous separation system. A flowmeter 30 is also provided.

Preferably, a single pressurized gas source 31 supplies each of the pulse dampeners 12, 14, 18 and 22 with pressurized gas, such as nitrogen gas. The source 31 has separate lines 32, 33, 34 and 35 controlled by separate gas pressure regulators 36, 37, 38 and 39. In this way, each pulse dampener is supplied by one source of pressurized gas. The purpose of the pressurized gas will be discussed in detail below with respect to FIGS. 2-4.

As is known, the chromatography system separates component "a" from component "B" in the feed stream from the feed stream source 20. The columns 25-29 contain an adsorbent material that exhibits a stronger bond for component "A" than component "B". Therefore, a longer retention time on the adsorbent will be exhibited by component "A " than component "B" and a separation can be effected.

Continuous separation of component "A " from a mixture of component "A" and "B" is accomplished by introducing a mixture of component "A" and component "B" from feed stream 20 into an eluant stream from eluant source 16 continuously circulating in the system. The eluant is circulated by means of the reciprocating pump 10. As the internal recirculating eluant flow carries the component "A" and component "B" mixture downstream from its introduction point through the adsorbent, component "A" is adsorbed allowing component "B" to move downstream ahead of component "A". After a period of time, the component "B" will progress through one column section and proceed to the succeeding section. The feed stream 20 will then be advanced to the next column to maintain the feed stream 20 between the advancing component "B" and the component "A" lagging behind. In this manner, the component "A" and component "B" mixture is continuously separated into a component "A" rich product and a component "B" by-product. The component "B" by-product stream is removed downstream of the feed source 20, as at point 42 and the component "A" rich product stream is removed just upstream of the feed source 20 as at point 40.

The pulse dampeners 12, 14, 18 and 22 are used to smooth the flow of the eluant and the mixture of component "A" and component "B" through the system. By "smooth" is meant the flow rate of the eluant can be accurately measured by the flowmeter 30 and the pressure swings of the eluant are reduced through the system, smoothing the process flow to provide more precise process control.

Figure 2:
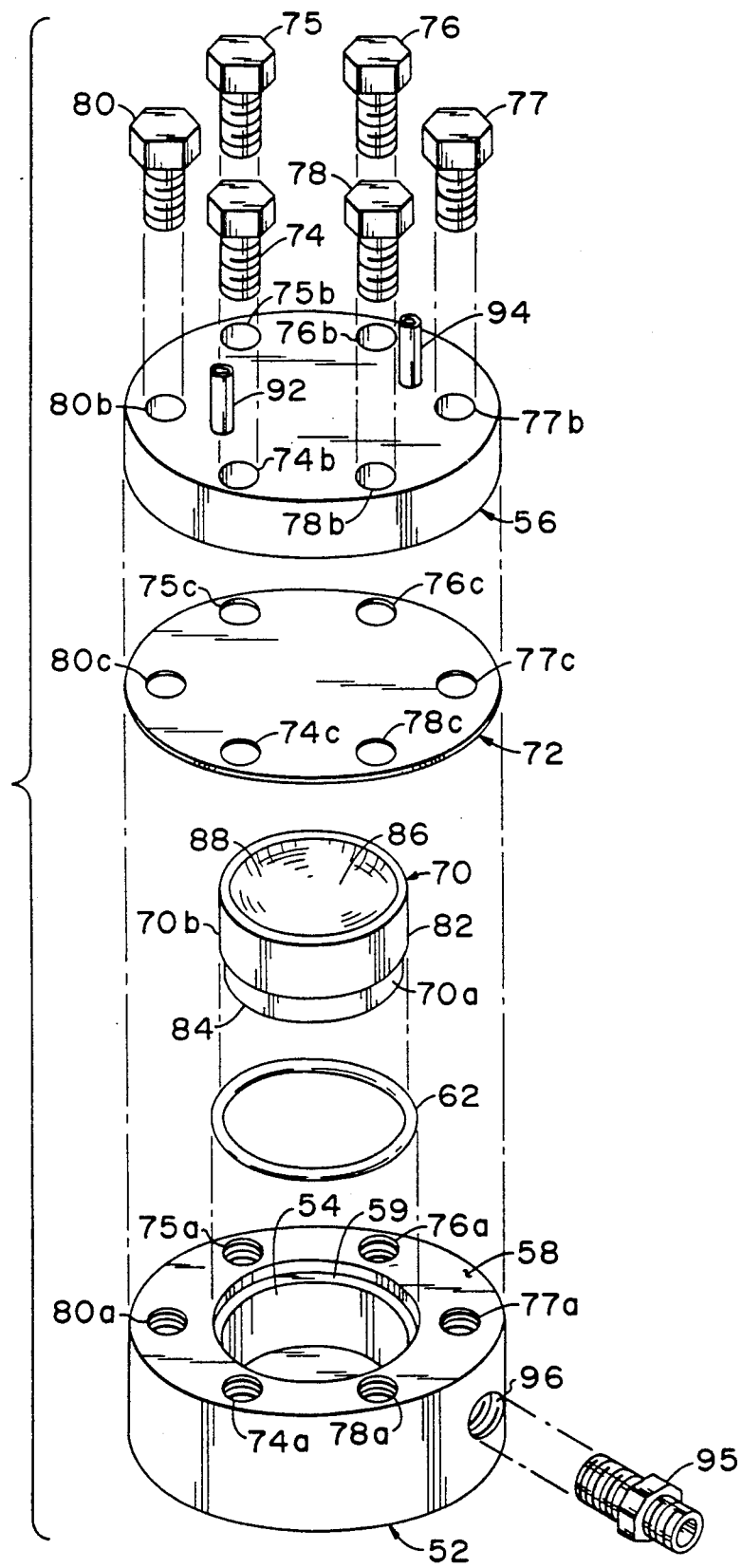
FIG. 2 is an exploded perspective view of the pulse dampener of the invention.
Figure 3:
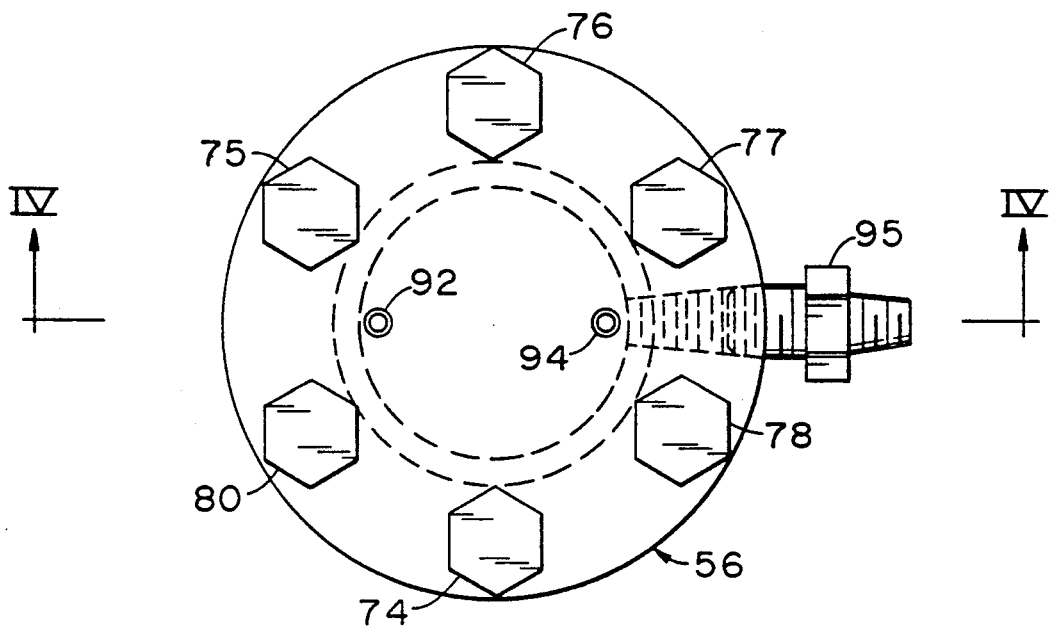
FIG. 3 is a top plan view of the pulse dampener of the invention.
Figure 4:
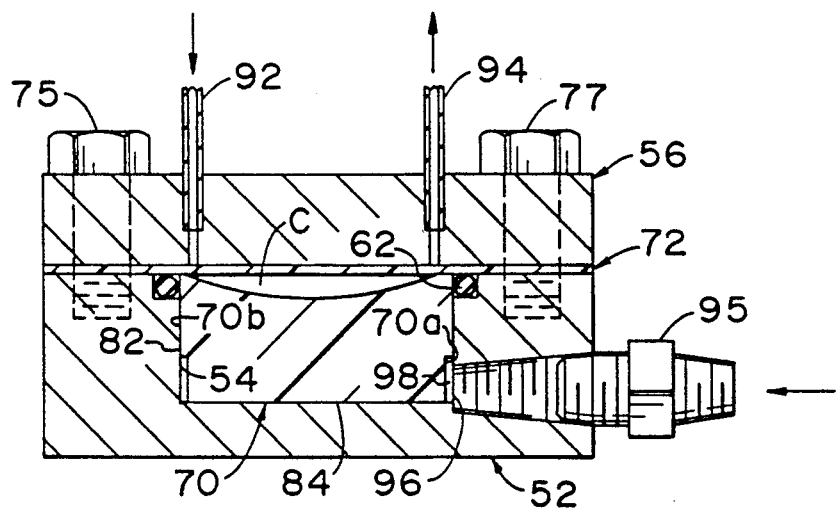
FIG. 4 is a cross-sectional view taken along line IV—IV of FIG. 3.

Referring more particularly to FIGS. 2–4, an embodiment of the pulse dampener of the invention is shown. The pulse dampener consists of a generally cylindrical body 52 having a generally cylindrical and upwardly open cavity 54 formed therein and a generally cylindrical cover 56. The open end of the cavity is preferably a generally flat surface 58, the inner extremity of which is stepped down annularly to form rim 59. The annular rim 59 comprises a seat which receives and supports a resilient seal 62. The body 52 and cover 56 are preferably made of stainless steel but can be carbon steel or plastic.

A cavity insert 70 (explained in detail hereinbelow) is disposed in the cavity 54. A diaphragm 72 of greater dimension than the cavity opening is positioned with its outer portions in overlying contact with surface 58 so as to permit sealing of the cavity 54 by the cover 56. The diaphragm 72 is supported and clamped tightly over the cavity 54 when the cover 56 is affixed to the body 52. The diaphragm 72 is made of any elastomer with tetrafluoroethylene being the preferred material.

As can be seen in FIGS. 2 and 3, the cover 56 is clamped to the body 52 by six screws 75, 76, 77, 78, 79 and 80. The body 52 and cover 56 have defined screw holes 75a–80a and 75b–80b respectively that receive the screws 75–80. The diaphragm 72 also has holes 75c–80c which correspond to the screw holes in the cover 56 and the body 52.

The insert 70 in the form shown is made of plastic and is disposed in the cavity 54. The insert 70 is cylindrical in shape having a sidewall 82, a base wall 84 and a top wall 86. The insert top wall 86 forms a recess 88. The top wall 88 is concave but can be any recessed shape. The radius of curvature of the top wall can be anywhere from one to four inches. It will be appreciated that the diaphragm and the recess 88 define a chamber "C" (See FIG. 4).

The cover 56 is provided with an inlet means 92 and an outlet means 94, where the liquid is pumped into and out of the pulse dampener. The inlet means 92, the chamber "C" and the outlet means 94 form a liquid flow path for the liquid pumped through the pulse dampener.

It will be appreciated that in an alternate embodiment of the device chamber "C" can be formed by a cavity defined by the body and the diaphragm 72 only without the need for an insert 70.

The body 52 also has a gas inlet means 95 which communicates with the cavity 54 for providing gas from the gas source 31 (See FIG. 1). The gas is preferably an inert compressed gas such as nitrogen, although any inert gas can be used. As can be seen in FIG. 4, gas from the gas inlet means 95 enters the cavity 54 through an opening 96 in the base of the cavity 54 and is transported in a annular passageway 98 and then up along the interface formed by sidewall of the body 52 and the sidewall 82 of insert 70. The insert 70 also has a radially restricted portion 70a that communicates with the gas inlet means 95. The insert 70 has a further radially enlarged portion 70b overlying the radially restricted portion 70a to further defined passageway 98 and the interface between body 52 and insert 70 for passing gas to chamber "C". The radially enlarged portion 70b has a greater diameter than the radially restricted portion 70a, with radially enlarged portion shown in FIG. 4 having a diameter of 1 15/32 inches and radially restricted portion shown in FIG. 4 having a diameter of about 1 7/16 inches as shown in FIGS. 2–4.

In operation, the gas flows from the gas source 31 (FIG. 1) through the gas inlet means 95 into passageway 98 and up through the interface formed by a loose fit between body 52 and insert 70 to chamber "C". This provides the cushioning for the liquid flowing through the pulse dampener. The volume of the chamber "C" is approximately equal to the volume of liquid pumped by one stroke of the reciprocating pump of the pumping system. This relationship is desired because a chamber "C" volume smaller than the volume of liquid pumped by one stroke will limit the dampening ability of the pulse dampener whereas a chamber "C" volume greater than the volume of liquid pumped by one stroke may allow pockets in the chamber "C" which are not continuously flushed ("dead space"). This "dead space" is undesired, because of mixing of the eluant and the feed source which may occur and because of the possibility of bacteria growth in this dead space.

The gas delivery means 31 (FIG. 1) provides a gas under pressure to the cavity 54 and in turn into the chamber "C". The gas pressure provided to chamber "C" is such as to provide a smooth liquid flow in the pumping system. The gas pressure provided to chamber "C" preferably ranges from about eighty-five percent (85%) to about one hundred fifteen percent (115%) of the average of (i) the high pressure of the liquid flow in the liquid outlet means 94 before gas pressure is introduced into the pulse dampener and (ii) the low pressure of the liquid flow in the liquid outlet means 94 before gas pressure is introduced into the pulse dampener. More preferably, the gas pressure provided to chamber "C" is generally equal to the average of the (i) high and (ii) low pressure discussed above. The gas pressure provided to chamber "C" will be discussed further hereinafter in Examples I and II.

In operation, a liquid is introduced through the inlet means 92 and is collected on top of the diaphragm 72. The gas is introduced into the pulse dampener via gas inlet means 95 from gas source 31. It will be appreciated that gas may be introduced into the pulse dampener either before or after liquid flow is initiated. As the amount of liquid introduced to the pulse dampener increases, the enclosed fluid in chamber "C" is compressed and the diaphragm 72 bends towards the top wall 86 of the insert 70. This is desired since the enlargement corresponds to the liquid maximally delivered by pump 10 during one cycle. The pulse dampener stores a part of the volume delivered by pump 10 during the feeding of liquid into the pulse dampener and outputs this part of the remaining segment of the pump cycle, i.e., that part of the pump cycle when no liquid is pumped.

The method of the invention comprises providing a pulse dampener as shown in FIGS. 2-4, establishing a flow of liquid through the liquid inlet, across the diaphragm and out the liquid outlet and introducing a gas into the gas inlet means of the pulse dampener and then into the chamber formed by the insert and the diaphragm. The gas is supplied at a predetermined pressure that will provide a smooth liquid flow in the pumping system. The predetermined pressure ranges from about eighty-five percent (85%) to one hundred fifteen percent (115%) of the average of (i) the high pressure of the liquid flow in the liquid outlet means 94 before gas pressure is introduced into the pulse dampener and (ii) the low pressure of the liquid flow in the liquid outlet means 94 before gas pressure is introduced into the pulse dampener.

The method further comprises providing the insert 70 having the radially restricted portion 70a and radially enlarged portion 70b to further define the passageway between the cavity and the insert. The method also comprises providing that the chamber "C" is defined by the insert and the diaphragm and that the chamber volume is generally equal to the volume of liquid pumped by one stroke of the reciprocating pump.

EXAMPLE I

A pulse dampener embodying the invention was used in a system having a reciprocating pump and a flowmeter. The reciprocating pump 10 pumped liquid through the inlet means 92 of the pulse dampener. The pump 10 operated at 25% motor speed and had a stroke length of 10 mm. The liquid pumped was deionized water. A liquid flow was initiated at the inlet means 92, across the diaphragm 72 and out the liquid outlet means 94. The pressure of the liquid emerging from the outlet means 94 of the pulse dampener was measured. Nitrogen gas was delivered to the pulse dampener through the gas inlet means 95 of the pulse dampener through the passageway 98 and into the chamber "C". The gas pressure was controlled by a pressure regulator, such as regulator 36.

The liquid pressure flowing into the pulse dampener from the reciprocating pump had a range of liquid pressure from 50-137 psi. This liquid flow was first introduced into the pulse dampener without initiating any gas flow into the chamber. The range of the liquid pressures at the outlet means 94 was measured after the liquid flow was stabilized (approximately 1 minute). The low pressure was 50 psi and the high pressure was 61 psi. Subsequently, the chamber "C" was charged with gas pressure of 10 psi. Again the low and high pressures were measured (after stabilization of the liquid flow) and found to be 49 psi and 62 psi, respectively. The gas pressure in the chamber was incrementally increased and the low and high pressures were measured and recorded.

Table I lists in the left column the $N_2$ pressure established in chamber "C" of the pulse dampener. The right column lists the low and high liquid pressure at the outlet means 94 for each respective $N_2$ pressure in the chamber "C". For example, at 50 psi of $N_2$ pressure, the liquid pressure at the outlet means 94 went from a low of 50 psi to a high of 60 psi or a range of 10 psi.

TABLE I

| $N_2$ Pressure (psi) | Liquid Pressure (psi) |
| --- | --- |
| 0 | 50-61 |
| 10 | 49-62 |
| 20 | 48.5-62 |
| 30 | 49-62 |
| 40 | 49-61.5 |
| 50 | 50-60 |
| 55 | 54-55 |
| 60 | 51-58 |
| 70 | 51-58.5 |
| 80 | 51-59.5 |

The $N_2$ pressure which provided the smoothest flow (i.e., smallest range from the high pressure reading to the low pressure reading) was at 55 psi. At 55 psi, the liquid pressure at the outlet means went from a low reading of 54 psi to a high reading of 55 psi, or a range of 1 psi. This is an extremely smooth flow. The optimum pressure for charging chamber "C" is found by taking the average of the low and high liquid pressure readings at the liquid outlet means 94 when no gas pressure is being charged into chamber "C". In this case, at 0 psi, the low liquid pressure reading was 50 psi and the high liquid pressure reading was 61 psi. The average of these two values is approximtely 55 psi. At 55 psi of $N_2$ pressure, as was discussed above, the smoothest flow was obtained.

EXAMPLE II

The experiment was continued only with a higher liquid pressure exerted from the reciprocating pump.

TABLE II

| $N_2$ Pressure (psi) | Liquid Pressure (psi) |
| --- | --- |
| 0 | 100-136 |
| 20 | 100-137.5 |
| 40 | 100-138 |
| 60 | 100-137.5 |
| 80 | 101-137 |
| 90 | 102-136 |
| 95 | 102.5-135.5 |
| 100 | 103.5-135 |
| 110 | 110-130.5 |
| 115 | 114.5-124 |
| 118 | 116-118.5 |
| 120 | 114.5-120 |
| 130 | 103-129 |
| 140 | 102-134.5 |

In this case, the low liquid pressure reading was 100 psi and the high liquid pressure reading is 136 psi when the chamber "C" was not charged with $N_2$ pressure. The average of the low and high liquid pressure readings is approximately 118 psi. At 118 psi of N pressure, the low liquid pressure reading was 116 psi and the high liquid pressure reading was 118.5 psi or a range of 2.5 psi. This was the smallest range of the liquid pressure readings observed in Example II.

It will be appreciated that a pulse dampener useful in chromatography systems operating at low liquid pressures is provided. The pulse dampener includes a gas source that delivers a cushioning fluid to a chamber inside the pulse dampener to insure a smooth liquid flow at the outlet of the pulse dampener. An associated method is also provided.

Whereas a particular embodiment of the invention has been described above, for purposes of illustration, it will be evident to those skilled in the art that numerous variations of the details may be made without departing from the invention as defined in the appended claims.

What is claimed is:

1. A pulse dampener for reducing the effect of pulsations of liquid flowing in a flow line of a pumping system including a reciprocating pump, said pulse dampener comprising:

a housing defining an inside cavity and having a flow line inlet, a flow line outlet and a gas delivery opening;

a resilient diaphragm separating said cavity into a flow line subcavity and a dampening subcavity; and gas delivery means for providing gas to said dampening subcavity at an average pressure of (i) the high pressure of said liquid flow in said flow line outlet before said gas pressure is introduced into said pulse dampener and (ii) the low pressure of said liquid flow in said flow line outlet before said gas pressure is introduced into said pulse dampener.

2. The pulse dampener of claim 1, wherein said gas is provided at a pressure that ranges from about eighty-five percent (85%) to one hundred fifteen percent (115%) of the average of (i) the high pressure of said liquid flow in said flow line outlet before said gas pressure is introduced into said pulse dampener and (ii) the low pressure of said liquid flow in said flow line outlet before said gas pressure is introduced into said pulse dampener.

3. A pulse dampener to reduce the effect of the pulsations of liquid flowing in a chromatography system including a reciprocating pump, said pulse dampener comprising:

a body having a cavity formed therein;

a cover for sealed connection with said body; and a diaphragm secured between said body and said cover for sealing said cavity from said cover;

said cover having a liquid inlet means and a liquid outlet means;

said cover and said diaphragm cooperating to define a liquid flow path through said liquid inlet means, across said diaphragm and out said liquid outlet means;

said body having gas inlet means for receiving a gas into said cavity;

said cavity and said diaphragm defining a chamber for receiving said gas; and gas delivery means for providing gas to said cavity at an average pressure of (i) the high pressure of said liquid flow in said liquid outlet means before gas pressure is introduced into said pulse dampener and (ii) the low pressure of said liquid flow in said liquid outlet means before said gas pressure is introduced into said pulse dampener.

4. The pulse dampener of claim 3, wherein said predetermined gas pressure ranges from about eighty-five percent (85%) to about one hundred fifteen percent (115%) of the average of (i) the high pressure of said liquid flow in said liquid outlet means before said gas pressure is introduced into said pulse dampener and (ii) the low pressure of said liquid flow in said liquid outlet means before said gas pressure is introduced into said pulse dampener.

5. The pulse dampener of claim 3, wherein said diaphragm being of greater dimension than said cavity so that when said diaphragm is secured between said body and said cover, said cavity will be sealed by said diaphragm.

6. The pulse dampener of claim 5, including an non-compressible insert disposed in said cavity, said insert having a recessed portion cooperating with said diaphragm to define said chamber.

7. The pulse dampener of claim 6, wherein said insert and cavity define a passageway for allowing said gas to reach said chamber.

8. The pulse dampener of claim 7, wherein a portion of said insert is radially restricted so as to define an area in communication with said gas inlet means.

9. The pulse dampener of claim 8, wherein a portion of said insert has a radially enlarged portion overlying said radially restricted portion to further define said passageway.

10. A method of dampening the pulsations of liquid flowing in a pumping system including a reciprocating pump, said method comprising the steps of:

providing pulse dampener means including (i) a cover having a liquid inlet means and a liquid outlet means, (ii) a body having a cavity formed therein, said body including a gas inlet means communicating with said cavity, and (iii) a diaphragm secured between said body and said cover to cooperate with said body in sealing said cavity;

establishing flow of said liquid through said liquid inlet means, across said diaphragm and out said liquid outlet means; and introducing a gas into said gas inlet means, said gas having an average pressure of (i) the high pressure of said liquid flow in said liquid outlet means before said gas pressure is introduced into said pulse dampener and (ii) the low pressure of said liquid flow in said liquid outlet means before said gas pressure is introduced into said pulse dampener.

11. The method of claim 10, wherein employing said gas at a pressure that ranges from about eighty-five percent (85%) to about one hundred fifteen percent (115%) of the average of (i) the high pressure of said liquid flow in said liquid outlet means before said gas pressure is introduced into said pulse dampener and (ii) the low pressure of said liquid flow in said liquid outlet means before said gas pressure is introduced into said pulse dampener.

12. The method of claim 10, including providing an non-compressible insert having a recessed portion; and placing said insert in said cavity, whereby a sealed chamber is formed by said diaphragm and said insert.

13. The method of claim 12, including transporting said gas from said gas inlet means to said chamber by means of a passageway defined by said cavity and said insert.

14. The method of claim 13, including providing said insert having a radially restricted portion so as to define an area in communication with said gas inlet means and providing said insert having a radially enlarged portion overlaying said radially restricted portion to further define said passageway.

15. A pulse dampener for reducing the effect of pulsations of liquid flowing in a flow line of a pumping system including a reciprocating pump, said pulse dampener comprising:
- a housing defining an inside cavity and having a flow line inlet, a flow line outlet and a gas delivery opening;
- a resilient diaphragm separating said cavity into a flow line subcavity and a dampening subcavity having a volume generally equal to the volume of liquid pumped by one stroke of said reciprocating pump; and
- gas delivery means for providing gas to said dampening subcavity at a pressure such that there is substantially smooth liquid flow in said pumping system.

16. A pulse dampener to reduce the effect of the pulsations of liquid flowing in a chromatography system including a reciprocating pump, said pulse dampener comprising:
- a body having a cavity formed therein;
- a cover for sealed connection with said body; and
- a diaphragm secured between said body and said cover for sealing said cavity from said cover;
- said cover having a liquid inlet means and a liquid outlet means;
- said cover and said diaphragm cooperating to define a liquid flow path through said inlet means, across said diaphragm and out said liquid outlet means;
- said body having gas inlet means for receiving a gas into said cavity;
- said cavity and said diaphragm defining a chamber for receiving said gas wherein the volume of said chamber is generally equal to the volume of liquid pumped by one stroke of said reciprocating pump; and
- gas delivery means for providing said gas to said cavity at a pressure such that there is a substantially smooth liquid flow in said pumping system.

17. The pulse dampener of claim 16, wherein said diaphragm has greater dimension than said cavity so that when said diaphragm is secured between said body and said cover, said cavity will be sealed by said diaphragm.

18. The pulse dampener of claim 17, including an insert disposed in said cavity, said insert having a recessed portion cooperating with said diaphragm to define said chamber.

19. The pulse dampener of claim 18, wherein said insert and said cavity define a passageway for allowing said gas to reach said chamber.

20. The pulse dampener of claim 19, wherein a portion of said insert is radially restricted so as to define an area in communication with said gas inlet means.

21. The pulse dampener of claim 20, wherein a portion of said insert has a radially enlarged portion overlying said radially restricted portion to further define said passageway.

22. A method of dampening the pulsations of liquid flowing in a pumping system including a reciprocating pump, said method comprising the steps of:
- providing pulse dampener means including (i) a cover having a liquid inlet means and a liquid outlet means, (ii) a body having a cavity formed therein, said body including a gas inlet means communicating with said cavity, and (iii) a diaphragm secured between said body and said cover to cooperate with said body in sealing said cavity;
- providing in said cavity a chamber having a volume generally equal to the volume of liquid pumped by one stroke of said reciprocating pump;
- establishing flow of said liquid through said liquid inlet means, across said diaphragm and out said liquid outlet means; and
- introducing a gas into said gas inlet means, said gas having a pressure such that there is a substantially smooth liquid flow in said system.

23. The method of claim 22, including providing an insert having a recessed portion; and placing said insert in said cavity, whereby a sealed chamber is formed by said diaphragm and said insert.

24. The method of claim 23, including transporting said gas from said gas inlet means to said chamber by means of a passageway defined by said cavity and said insert.

25. The method of claim 24, including providing said insert having a radially restricted portion so as to define an area in communication with said gas inlet means and providing said insert having a radially enlarged portion overlying said restricted portion to further define said passageway.

* * * * *

UNITED STATES PATENT AND TRADEMARK OFFICE
CERTIFICATE OF CORRECTION

PATENT NO. : 5,171,134

DATED : December 15, 1992

INVENTOR(S) : Morgart et al

It is certified that error appears in the above-identified patent and that said Letters Patent is hereby corrected as shown below:

| | |
|---|---|
| Column 2, line 54: | After "component", change "a" to |
| Column 4, line 11: | After "the interface formed by" and before "sidewall of the body", add --the--. |
| Column 4, line 11 | After "of the body 52" and before "and the sidewall 82", insert --(which forms the cavity 54)--. |
| Column 4, line 16: | After "to further" and before "passageway", change "defined" to --define--. |
| Column 6, line 59: | Change "Npressure" to --$N_2$ pressure--. |

UNITED STATES PATENT AND TRADEMARK OFFICE
CERTIFICATE OF CORRECTION

PATENT NO. : 5,171,134

DATED : December 15, 1992

INVENTOR(S) : Morgart et al

It is certified that error appears in the above-identified patent and that said Letters Patent is hereby corrected as shown below:

Column 8,
  In Claim 7, line 2:   After "said insert and" and before "cavity define a passageway", insert --said--.

Column 9,
  In Claim 16, line 12:   After "a liquid flow path through said" and before "inlet means," insert --liquid--.

Column 10,
  In Claim 25, line 6:   After "overlying said" and before "restricted portion", insert --radially--.

Signed and Sealed this

Seventh Day of December, 1993

Attest:

BRUCE LEHMAN

Attesting Officer    Commissioner of Patents and Trademarks